United States Patent [19]

Allais et al.

[11] 4,233,305
[45] Nov. 11, 1980

[54] NOVEL DERIVATIVES OF 2-(4-QUINOLINYLAMINO)-5-FLUORO-BENZOIC ACIDS

[75] Inventors: André Allais, Gagny; Jean Meier, La Varenne Saint-Hilaire; Roger Deraedt, Les Pavillons-sous-Bois, all of France

[73] Assignee: Roussel Uclaf, Paris, France

[21] Appl. No.: 966,964

[22] Filed: Dec. 6, 1978

[30] Foreign Application Priority Data

Dec. 15, 1977 [FR]  France ................................ 77 37835
Dec. 15, 1977 [FR]  France ................................ 77 37836

[51] Int. Cl.³ ...................... A61K 31/47; C07D 215/44
[52] U.S. Cl. ............................... 424/258; 424/248.55; 424/250; 544/128; 544/363; 546/161
[58] Field of Search ............... 546/161; 544/128, 363; 424/248.55, 250, 258

[56] References Cited

U.S. PATENT DOCUMENTS

| | | | |
|---|---|---|---|
| 3,150,047 | 9/1964 | Allais et al. | 546/161 |
| 3,151,026 | 9/1964 | Allais et al. | 544/128 |
| 3,232,944 | 2/1966 | Allais et al. | 424/258 |
| 3,644,368 | 2/1972 | Allais et al. | 424/258 |
| 3,790,578 | 2/1974 | Theriault et al. | 546/161 |
| 3,910,922 | 10/1975 | Allais et al. | 546/161 |
| 3,935,229 | 1/1976 | Giudicelli et al. | 544/363 |
| 3,971,789 | 7/1976 | Archibald et al. | 546/161 |

Primary Examiner—Paul M. Coughlan, Jr.
Attorney, Agent, or Firm—Hammond & Littell, Weissenberger and Muserlian

[57] ABSTRACT

Derivatives of 2-(4-quinolinylamino)-5-fluorobenzoic acid compounds of the formula

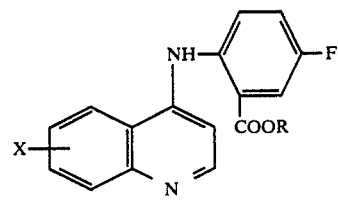

I wherein X is selected from the group consisting of chlorine and —CF₃ in the 7- or 8-position and R is selected from the group consisting of hydrogen, an esterifying group, alkali metals, alkaline earth metals, ammonium and non-toxic, pharmaceutically acceptable organic amines and their non-toxic, pharmaceutically acceptable acid addition salts having remarkable analgesic properties and their preparation.

21 Claims, No Drawings

NOVEL DERIVATIVES OF 2-(4-QUINOLINYLAMINO)-5-FLUORO-BENZOIC ACIDS

STATE OF THE ART

Related art in the present field includes U.S. Pat. No. 3,232,944 and 3,644,368, and Swiss Pat. No. 548,973 as well as the article at Chimie Therapeutique, Vol. 8 (1973), p. 154–168. French Pat. No. 2,181,807 and its patent of addition No. 2,298,330 describe as intermediates compounds of the formula

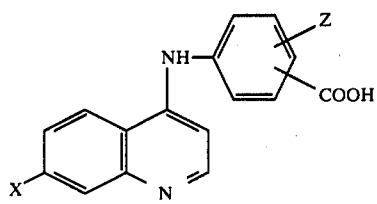

wherein X is halogen such as chlorine or —CF$_3$ and Z is halogen such as chlorine or bromine but they do not describe any compounds wherein Z is fluorine.

OBJECTS OF THE INVENTION

It is an object of the invention to provide the novel compounds of formula I and their non-toxic, pharmaceutically acceptable acid addition salts and a novel process for their preparation.

It is another object of the invention to provide novel analgesic compositions and a novel method of relieving pain in warm-blooded animals.

These and other objects and advantages of the invention will become obvious from the following detailed description.

THE INVENTION

The novel products of the invention are selected from the group consisting of 2-(4-quinolinylamino)-5-fluorobenzoic acid compounds of the formula

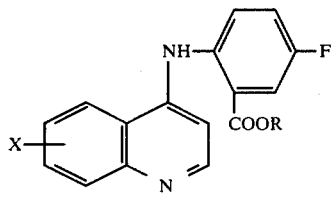

wherein X is selected from the group consisting of chlorine and —CF$_3$ in the 7- or 8-position and R is selected from the group consisting of hydrogen, an esterifying group, alkali metals, alkaline earth metals, ammonium and non-toxic, pharmaceutically acceptable organic amines and their non-toxic, pharmaceutically acceptable acid addition salts.

Examples of R are hydrogen, ammonium, alkali metals such as sodium, potassium or lithium, alkaline earth metals such as calcium, non-toxic, pharmaceutically acceptable organic amines such as triethylamine, diethylamine, substituted or non-substituted aminoalcohols, lysine, arginine and choline and esterifying groups derived from alcohols containing 1 to 18 carbon atoms of the aliphatic, cycloaliphatic, aromatic or aromatic aliphatic alcohol series which may contain one or more heteroatoms, may optionally be substituted with alkylamines, dialkylamino, with one or more straight or branched chain unsaturated carbon groups, with one or more of hydroxy, alkoxy, amino and —CF$_3$, with one or more halogens or optionally substituted with one or more heterocycle groups which may optionally be substituted with one or more of the above substituents or with another heterocycle or with a phenyl optionally substituted with one or more of the above substituents.

Examples of suitable acids for the non-toxic, pharmaceutically acceptable acid addition salts are inorganic acids such as hydrochloric acid, hydrobromic acid, hydroiodic acid, phosphoric acid and sulfuric acid and organic acids such as formic acid, alkanesulfonic acids such as methanesulfonic acid and arylsulfonic acids such as p-toluenesulfonic acid.

Especially preferred among the compounds of formula I are those wherein R is hydrogen and the salts of the said acids; those wherein R is alkyl of 1 to 8 carbon atoms such as methyl, ethyl, propyl, isopropyl, butyl, isobutyl, n-pentyl and n-hexyl; those wherein R is

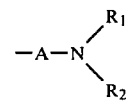

wherein A is branched alkylene of 3 to 5 carbon atoms or —(CH$_2$)$_n$— and n is a number of 2 to 5 and R$_1$ and R$_2$ are individually alkyl of 1 to 8 carbon atoms or together with the nitrogen atom to which they are attached form a heterocyclic selected from the group consisting of piperidinyl, pyrrolidinyl, morpholinyl and N-piperazinyl optionally substituted on the second nitrogen atom with alkyl of 1 to 4 carbon atoms with A preferably being ethylene or isopropylene and R$_1$ and R$_2$ being alkyl such as methyl, ethyl n-propyl or n-butyl; those wherein R has the formula

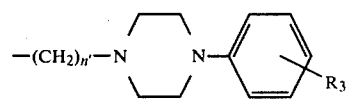

with R$_3$ being selected from the group consisting of hydrogen, halogen, —CF$_3$, —SCF$_3$, —OCF$_3$ and alkyl and alkoxy of 1 to 8 carbon atoms in the 2,3- or 4-position, n' is 2 to 5, preferably 2,3 or 4 and R$_3$ is preferably fluorine, chlorine, bromine, methyl, ethyl, n-propyl, n-butyl, methoxy, ethoxy, n-propoxy or n-butoxy; and those wherein R is

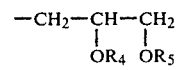

and R$_4$ and R$_5$ are both hydrogen or form a ketonide of the formula

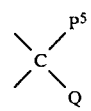

and P and Q are alkyl of 1 to 8 carbon atoms, aralkyl of 7 to 13 carbon atoms or aryl of 6 to 12 carbon atoms, preferably methyl, ethyl, benzyl or phenyl; and their non-toxic, pharmaceutically acceptable acid addition salts.

Especially preferred compounds of formula I are those wherein R is methyl,

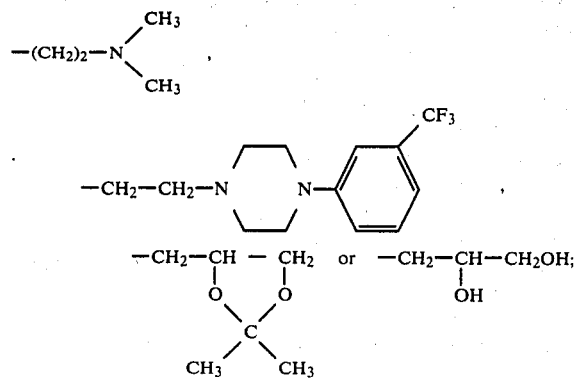

those wherein X is a 7-chloro; those wherein X is in the 8-position; and those wherein X is —CF$_3$; and their non-toxic, pharmaceutically acceptable acid addition salts.

The novel process of the invention for the preparation of compounds of formula I comprises reacting a compound of the formula

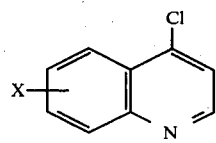

II wherein X is in the 7- or 8-position and is selected from the group consisting of chlorine and —CF$_3$ with a compound of the formula

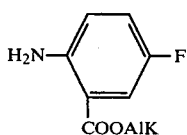

III wherein Alk is alkyl of 1 to 18 carbon atoms to obtain a compound of the formula

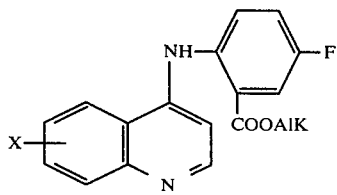

I$_A$ which may, if desired, be reacted with a saponification agent to obtain the corresponding free acid of the formula

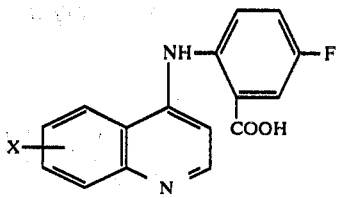

I$_B$ which, if desired, may be reacted with a base or acid to form the corresponding salt, or reacted with a transesterification agent to obtain the corresponding ester which may be reacted with an acid to form the acid addition salt or may, if desired, be reacted with an alcohol of the formula

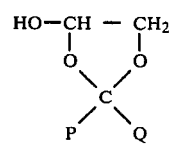

which is then reacted with an hydrolysis agent to obtain the corresponding 2,3-dihydroxypropyl ester which also may be reacted with an acid, if desired, to form the acid addition salt. In a preferred mode of the invention, AlK is methyl, ethyl, n-propyl or n-butyl and the condensation of the compounds of formulae II and III is effected in the presence of a mineral acid such as hydrochloric acid and the saponification agent is sodium hydroxide or potassium hydroxide. The transesterification is preferably effected with an alcohol in the presence of an alkaline agent such as an alkali metal hydride, alkali metal amide or an alkali metal alcoholate and is effected in an organic solvent at 50° to 200° C. The preferred acid hydrolysis agent is hydrochloric acid.

The transesterification process is especially useful with an alcohol of the formula TOH wherein T is alkyl of 1 to 8 carbon atoms such as methyl, ethyl, propyl, isopropyl, butyl, isobutyl, n-pentyl and n-hexyl; those wherein T is

wherein A is branched alkylene of 3 to 5 carbon atoms or —(CH$_2$)$_n$— and n is a number of 2 to 5 and R$_1$ and R$_2$ are individually alkyl of 1 to 8 carbon atoms or together with the nitrogen atom to which they are attached form a heterocyclic selected from the group consisting of piperidinyl, pyrrolidinyl, morpholinyl and N-piperazinyl optionally substituted on the second nitrogen atom with alkyl of 1 to 4 carbon atoms with A preferably being ethylene or isopropylene and R$_1$ and R$_2$ being alkyl such as methyl, ethyl, n-propyl or n-butyl; those wherein T has the formula

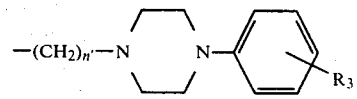

wherein $R_3$ being selected from the group consisting of hydrogen, halogen, —$CF_3$, —$SCF_3$, —$OCF_3$ and alkyl and alkoxy of 1 to 8 carbon atoms in the 2,3- or 4-position, n' is 2 to 5, preferably 2,3 or 4 and $R_3$ is preferably fluorine, chlorine, bromine, methyl, ethyl, n-propyl, n-butyl, methoxy, ethoxy, n-propoxy or n-butoxy; and those wherein T is

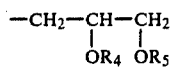

and $R_4$ and $R_5$ are both hydrogen or form a ketonide of the formula

and P and Q are alkyl of 1 to 8 carbon atoms, aralkyl of 7 to 13 carbon atoms or aryl of 6 to 12 carbon atoms, preferably methyl, ethyl, benzyl or phenyl; and their non-toxic, pharmaceutically acceptable acid addition salts.

The starting compounds of formula III are known and may be prepared by the process of French Pat. Nos. 1,514,280 or 1,584,746, for example. The alkyl 2amino-5-fluoro-benzoates are generally known and may be prepared by the process described in Castle et al, J. Heterocyclischen, Vol. 2 (1965), p. 459, for example.

The novel analgesic compositions of the invention are comprised of an analgesically effective amount of at least one compound of formula I and its non-toxic, pharmaceutically acceptable acid addition salts and an inert pharmaceutical carrier or excipient. The compositions may be in the form of tablets, dragees, gelules, granules, suppositories, injectable solutions or suspensions, pomades, cremes, gels and aerosol preparations prepared in the usual manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants, or emulsifiers and preservatives.

The compositions are useful for the treatment of muscular, articular or nervous pains; migraines or dental pain. Preferred active ingredients are methyl 2-(7-chloro-4-quinolinylamino)-5-fluoro-benzoate, (2,2-dimethyl-4-dioxalyl)-methyl 2-(8-trifluoromethyl-4-quinolinylamino)-5-fluoro-benzoate, 2-dimethylaminoethyl 2-(8-trifluoromethyl-4-quinolinylamino)-5-fluorobenzoate and its hydrochloride, 2-[4-(3-trifluoromethylphenyl)-piperazin-1-yl]-ethtyl 2-(8-trifluoromethyl-4-quinolinylamino)-5-fluoro-benzoate and its hydrochloride, and 2,3-dihydroxypropyl 2-(8-trifluoromethyl-4-quinolinylamino)-5-fluoro-benzoate.

The novel method of the invention for relieving pain in warm-blooded animals, including humans, comprises administering to warm-blooded animals an analgesically effective amount of at least one compound of formula I and its non-toxic, pharmaceutically acceptable acid addition salts. The compounds may be administered orally, rectally, parenterally or locally by topical application to the skin and mucous. The usual daily dose is 0,4 to 40 mg/kg depending on the compound and the method of administration. For example, the compounds of Examples 1 or 14 may be orally administered daily at 4 to 24 mg/kg.

In the following examples there are described several preferred embodiments to illustrate the invention. However, it should be understood that the invention is not intended to be limited to the specific embodiments.

EXAMPLE 1 methyl 2-(7-chloro-4-quinolinylamino)-5-fluoro-benzoate

A solution of 11.7 g of 4,7-dichloroquinoline, 10 g of methyl 2-fluoro-benzoate and 60 ml of 2 N hydrochloric acid was heated to reflux and was then iced and vacuum filtered. The recovered precipitate was dissolved in 250 ml of methanol and sufficient triethylamine was added to the solution to make it alkaline. The mixture was iced and filtered and the recovered product was washed with methanol and dried to obtain 12.2 g of methyl 2-(7-chloro-4-quinolinylamino)-5-fluoro-benzoate melting at 180° C.

EXAMPLE 2

2-(7-chloro-4-quinolinylamino)5-fluoro-benzoic acid

A solution of 1.8 g of the ester of Example 1, 25 ml of N sodium hydroxide solution, 25 ml of water and 100 ml of methanol was heated at 70°–75° C. for 90 minutes and the methanol was then evaporated. 100 ml of water and 10 ml of dimethylformamide were added to the mixture which was then heated to reflux. 4 ml of acetic acid were added thereto and the mixture was held in an ice bath for an hour and was then vacuum filtered. The recovered crystals were washed with water and dried to obtain 1.715 g of 2-(7-chloro-4-quinolinylamino)-5-fluoro-benzoic acid melting at 341°–342° C.

EXAMPLE 3

2-dimethylaminoethyl 2-(7-chloro-4-quinolinylamino)-5-fluorobenzoate and its hydrochloride A mixture of 4 g of the ester of Example 1, 2.45 ml of dimethylaminoethanol and 50 ml of anhydrous toluene was heated to reflux and then cooled to 50° C. and 95 mg of a 50% sodium hydride oil suspension was added thereto. The mixture was again heated to reflux and was then cooled to 40° C. and 0.2 ml of acetic acid were added thereto. The mixture was evaporated to dryness and the residue was dissolved in methylene chloride. The solution was filtered and the filtrate was washed with water, dried and filtered. The filtrate was evaporated to dryness to obtain 4.01 g of 2-dimethylaminoethyl 2-(7-chloro-4-quinolinylamino)-5-fluorobenzoate.

The said product was dissolved in 12 ml of ethanol and 1.52 ml of an anhydrous ethanol solution of 6.8 N hydrochloric acid and then 75 ml ofanhydrous ether were added thereto. The mixture was vacuum filtered and the crystals were washed with anhydrous ether and dried to obtain 3.73 g of 2-dimethylaminoethyl 2-(7-chloro-4-quinolinylamino)-5-fluoro-benzoate hydrochloride melting at 176° C.

EXAMPLE 4

2-[4-(3-trifluoromethylphenyl)-piperazin-1-yl]-ethyl 2-(7-chloro-4-quinolinylamino)-5-fluoro-benzoate and its dihydrochloride Using the procedure of Example 3, 4 g of the ester of Example 1 and 3.316 g of 2-[4-(3-trifluoromethylphenyl)-piperazin-1-yl]-ethanol were reacted to obtain 6.88 g of a raw oily product. 500 mg of the said product were crystallized from isopropyl ether to obtain 425 mg of 2-[4-(3-trifluoromethylphenyl)-piperazin-1-yl]-ethyl 2-(7-chloro-4-quinolinylamino)-5-fluoro-benzoate melting at 113° C.

6.375 g of the raw oily product were dissolved in 15 ml of absolute ethanol and 3.1 ml of an ethanolic solution of 6.8 N hydrochloric acid and then 75 ml of anhydrous ether were added thereto. The mixture stood at room temperature and was then vacuum filtered. The recovered crystals were washed with anhydrous ether and dried to obtain 6.92 g of raw product which is purified to give 6.395 g of the dihydrochloride of 2-/4-(3-trifluoromethylphenyl)-piperazin-1-yl/-ethyl 2-(7-chloro-4-quinolinylamino)-5-fluorobenzoate melting at 190° C.

EXAMPLE 5

(2,2-dimethyl-4-dioxalyl)-methyl 2-(7-chloro-4-quinolinylamino)-5-fluoro-benzoate Using the procedure of Example 3, 6 g of the ester of Example 1 and 4.8 g of glycerol acetonide were reacted to obtain 7.55 g of raw product which was purified to obtain 6.22 g of (2,2-dimethyl-4-dioxalyl)-methyl 2-(7-chloro-4-quinolylamino)-5-fluoro-benzoate melting at 92° C.

EXAMPLE 6

2,3-dihydroxypropyl 2-(7-chloro-4-quinolylamino)-5-fluorobenzoate

A solution of 5 g of the ester of Example 5 and 10 ml of aqueous 2 N hydrochloric acid was heated to reflux and was then iced and vacuum filtered. The recovered crystals were empasted with water and the mixture was vacuum filtered. The product was dissolved at 80° C. in 11 ml of dimethylformamide and 11 ml of water and 2.8 ml of triethylamine were added thereto. The mixture was iced and was vacuum filtered and the recovered crystals were washed with a 1—1 water-dimethylformamide mixture and were dried to obtain 4.3 g of product. The latter was dissolved in refluxing tetrahydrofuran and the mixture was filtered to remove insoluble. The filtrate was evaporated to dryness under reduced pressure and the residue was dissolved in refluxing methanol. The mixture was iced and vacuum filtered and the crystals were washed with iced methanol and dried to obtain 3.7 g of 2,3-dihydroxypropyl 2-(7-chloro-4-quinolinylamino)-5-fluorobenzoate melting at 168° C.

EXAMPLE 7

(2,2-dimethyl-4-dioxalyl)-methyl 2-(7-trifluoromethyl-4-quinolinylamino)-5-fluoro-benzoate STEP A: methyl 2-(7-trifluoromethyl-4-quinolinylamino)-5-fluoro-benzoate A mixture of 34.725 g of 4-chloro-7-trifluoromethyl-quinoline, 25.35 g of methyl 2-amino-5-fluoro-benzoate and 150 ml of 2 N hydrochloric acid was refluxed for 2½ hours and the aqueous phase was decanted. The gummy residue was dissolved in 150 ml of methanol containing 20% of water and triethylamine was added to the solution until it was alkaline. Crystallization occurred and the mixture was iced and vacuum filtered. The crystals were washed with water and dried to obtain 34.85 g of product which was crystallized from methanol to obtain 31.93 g of pure methyl 2-(7-trifluoromethyl-4-quinolinylamino)-5-fluoro-benzoate melting at 174° C.

STEP B: (2,2-dimethyl-4-dioxalyl)-methyl 2-(7-trifluoromethyl-4-quinolinylamino)-5-fluoro-benzoate A mixture of 9.1 g of the product of Step A, 6.6 g of 2,2-dimethyl-1,3-dioxolane-4-methanol and 90 ml of anhydrous toluene was refluxed for 90 minutes while removing the water of reaction and was then cooled to 60° C. 70 mg of a 50% sodium hydride-oil suspension were added thereto and the mixture was refluxed for another 2½ hours. The mixture was then cooled to 60° C. and 0.15 ml of acetic acid was added thereto. The mixture was evaporated to dryness under reduced pressure and the residue was dissolved in 250 ml of ether containing 20% of methylene chloride. The solution was washed with water, dried and evaporated to dryness to obtain 11.9 g of product which was crystallized from isopropyl ether to obtain 10.475 g of (2,2-dimethyl-4-dioxalyl)-methyl 2-(7-trifluoromethyl-4-quinolinylamino)-5-fluoro-benzoate melting at 118° C.

EXAMPLE 8

2,3-dihydroxypropyl 2-(7-trifluoromethyl-4-quinolinylamino)-5-fluoro-benzoate

A mixture of 9.28 g of the product of Example 7 in 20 ml of 2 N hydrochloric acid was refluxed for 15 minutes and the mixture was cooled in an ice bath for 2 hours. The mixture was decanted and the gummy residue was washed with ice water. Triethylamine was added to the aqueous phase until it was alkaline and the mixture was filtered. The recovered product was washed with water and dried to obtain 880 mg of a product melting at 168° C. The gummy product was dissolved in 10 ml of dimethylformamide and 12 ml of water and then 5.5 ml of triethylamine were added thereto. The mixture was cooled to 0° C. and was vacuum filtered. The recovered product was washed with water and dried to obtain 7.36 g of product melting at 167° C. The two products were crystallized from methanol to obtain 7.29 g of 2,3-dihydroxypropyl 2-(7-trifluoromethyl-4-quinolinylamino)-5-fluoro-benzoate melting at 167°–168° C.

EXAMPLE 9

2-[4-(3-trifluoromethylphenyl)-piperazin-1-yl]-ethyl 2-(7-trifluoromethyl-4-quinolinylamino)-5-fluoro-benzoate dihydrochloride Using the procedure of Step B of Example 7, 6.57 g of 4-(3-trifluoromethylphenyl)-piperazin-1-yl-ethanol and 9.19 g of methyl 2-(7-trifluoromethyl-4-quinolinylamino)-5-fluoro-benzoate were reacted to obtain 12.72 g of raw product which was chromatographed over silica gel. Elution with 95-5 methylene chloride-methanol mixture yielded 11.16 g of 2-[4-(3-trifluoromethylphenyl)-piperazin-1-yl]-ethyl 2-(7-trifluoromethyl-4-quinolinylamino)-5-fluoro-benzoate.
The said product was dissolved in 25 ml of hot absolute ethanol and then 5.6 ml of an ethanol solution of 6.6 N hydrochloric acid was added thereto at 50° C. The mixture was stirred and 60 ml of anhydrous ether were added thereto in small amounts. The mixture was stirred overnight at room temperature and after the addition of 0.5 ml of the ethanolic hydrochloric acid solution, the mixture was stirred for one hour and was vacuum filtered. The recovered crystals were washed with a 1-3 anhydrous ethanol-ether mixture and then with ether to obtain 11.7 g of the dihydrochloride of 2-[4-(3-trifluoromethylphenyl)-piperazin-1-yl]-ethyl 2-(7-trifluoromethyl-4-quinolinylamino)-5-fluoro-benzoate melting at 200° C.

EXAMPLE 10

2-dimethylaminoethyl 2-(7-trifluoromethyl-4-quinolinylamino)-5-fluoro-benzoate hydrochloride Using the procedure of Step B of Example 7, 3.56 g of dimethylamino ethanol were reacted to obtain, after crystallization of isopropyl ether, 7.35 g of raw 2-dimethylamino-ethyl 2-(7-trifluoromethyl-4-quinolinylamino)-5-fluorobenzoate. The said product was dissolved in anhydrous ethanol and 2.65 ml of ethanolic 6.6 N hydrochloric acid were added thereto. The mixture was cooled and was diluted with 15 ml of anhydrous ether and was vacuum filtered. The recovered product was washed with a 1-3 alcohol-ether mixture to obtain 6.94 g of product which was crystallized from anhydrous ethanol to obtain 4.12 g of pure dimethylaminoethyl 2-(7-trifluoromethyl-4-quinolinylamino)-5-fluorobenzoate hydrochloride melting at ≃220° C.

EXAMPLE 11 methyl 2-(8-trifluoromethyl-4-quinolinylamino)-5-fluorobenzoate

A solution of 16 g of 4-chloro-8-trifluoromethyl-quinoline, 11.62 g of methyl 2-amino-5-fluoro-benzoate and 70 ml of 2 N hydrochloric acid solution was heated to reflux and was allowed to stand overnight at room temperature. The mixture was iced and filtered and the product was empasted with a little water and was vacuum filtered. The recovered crystals were dissolved in methanol and triethylamine was added to the resulting solution until the pH was alkaline. The mixture was iced and filtered and the product was dried to obtain 11.2 g of methyl 2-(8-trifluoromethyl-4-quinolinylamino)-5-fluoro-benzoate melting at 166° C.

EXAMPLE 12

2-(8-trifluoromethyl-4-quinolinylamino)-5-fluoro-benzoic acid

A mixture of 1.45 g of the product of Example 11, 4 ml of 2 N sodium hydroxide solution and 21 ml of methanol was refluxed and the methanol was evaporated. 25 ml of water were added to the mixture and the solution was filtered through asbestos. The solution was heated to 60° C. and was acidified with concentrated hydrochloric acid. The resulting suspension was cooled and filtered and the recovered precipitate was washed with water and dried to obtain 1.26 g of 2-(8-trifluoromethyl-4-quinolinylamino)-5-fluoro-benzoic acid melting at 265°±3° C.

EXAMPLE 13

(2,2-dimethyl-4-dioxalyl)-methyl 2-(8-trifluoromethyl-4-quinolinylamino)-5-fluoro-benzoate A solution of 7 g of the ester of Example 11, 5.6 ml of the acetonide of anhydrous glycerol and 70 ml of toluene was refluxed for an hour and after the addition of 50 mg of sodium hydride in an oily suspension, the mixture was refluxed for another 3 hours. The mixture was evaporated to dryness under reduced pressure and the residue was taken up in 250 ml of refluxing isopropyl ether. The mixture was filtered through asbestos and ether was evaporated to obtain a volume of 75 ml. The mixture was iced overnight and was vacuum filtered. The product was empasted with iced isopropyl ether and was dried in an oven at 70° C. to obtain 6.9 g of (2,2-dimethyl-4-dioxalyl)-methyl 2-(8-trifluoromethyl-4-quinolinylamino)-5-fluoro-benzoate melting at 129°-130° C.

EXAMPLE 14

2-dimethylaminoethyl 2-(8-trifluoromethyl-4-quinolinylamino)-5-fluorobenzoate hydrochloride Using the process of Example 13, methyl 2-(8-trifluoromethyl-4-quinolinylamino)-5-fluoro-benzoate and dimethylamino-ethanol were reacted to form 2-dimethylaminoethyl 2-(8-trifluoromethyl-4-quinolinylamino)-5-fluorobenzoate which was then dissolved in ethanol. Dry hydrogen chloride in ethanol was added to the solution and anhydrous ether was added to effect precipitation. The mixture was vacuum filtered and the crystals were washed and dried to obtain 2-dimethylamino-ethyl 2-(8-trifluoromethyl-4-quinolinylamino)-5-fluoro-benzoate hydrochloride melting at 220° C.

EXAMPLE 15

2,3-dihydroxypropyl 2-(8-trifluoromethyl-4-quinolinylamino)-5-fluoro-benzoate

A solution of 5 g of the product of Example 13, 100 ml of ethanol, 10 ml of water and 2 ml of concentrated hydrochloric acid was heated to reflux and was then evaporated to dryness. The residue was taken up in water and the solution was stirred and filtered. The filtrate was adjusted to an alkaline pH by addition of 2 N hydroxide solution and the recovered product was empasted with water and then dried in an oven to obtain 4.5 g of crystals which were crystallized from butanol to obtain 3.9 g of 2,3-dihydroxypropyl 2-(8-trifluoromethyl-4-quinolinylamino)-5-fluorobenzoate melting at 197°-198° C.

EXAMPLE 16

2-[4-(3-trifluoromethylphenyl)-piperazin-1-yl]-ethyl 2-(8-trifluoromethyl-4-quinolinylamino)-5-fluoro-benzoate hydrochloride Using the procedure of Example 13, methyl 2-(8-trifluoromethyl-4-quinolinylamino)-5-fluoro-benzoate and 2-[-4-(3-trifluoromethylphenyl)-piperazin-1-yl]-ethanol were reacted to obtain 2-[4-3-trifluoromethylphenyl)-piperazin-1-yl]-ethyl 2-(8-trifluoromethyl-4-quinolinylamino)-5-fluorobenzoate. The said product was dissolved in absolute ethanol and an ethanolic solution of hydrogen chloride was added thereto followed by anhydrous ether. The mixture crystallized was vacuum filtered and the product was washed with anhydrous ether and was dried to form the desired hydrochloride salt melting at 230°-240° C.

EXAMPLE 17

2-dimethylamino-ethyl 2-(8-chloro-4-quinolinylamino)-5-fluorobenzoate hydrochloride

STEP A: methyl 2-(8-chloro-4-quinolinylamino)-5-fluorobenzoate

A mixture of 11.88 g of 4,8 dichloroquinoline, 10.4 g of methyl 2-amino-5-fluoro-benzoate and 60 ml of 2 N hydrochloric acid was refluxed for 2½ hours and was then cooled to ≃0° C. and vacuum filtered. The moist residue was dissolved in 125 ml of lukewarm methanol and triethylamine was added to the resulting solution to make the pH alkaline. The mixture stood overnight at room temperature and was vacuum filtered and the recovered product was washed with water and dried to obtain 8.3 g of raw product which was crystallized from methanol to obtain 7.39 g of methyl 2-(8-chloro-4-quinolinylamino)-5-fluoro-benzoate melting at 196° C.

STEP B: 2-dimethylamino-ethyl 2-(8-chloro-4-quinolinylamino)-5-fluoro-benzoate hydrochloride Using the procedure of Step B of Example 7, 6.61 g of the product of Step A and 4 ml of anhydrous 2-dimethylamino-ethanol were reacted to obtain 6.8 g of 2-dimethylamino-ethyl 2-(8-chloro-4-quinolinylamino)-5-fluoro-benzoate melting at 121°–122° C. 5.245 g of the said product were dissolved in 10 ml of anhydrous ethanol and 2.05 ml of an ethanol solution of 6.6 N hydrochloric acid were added thereto. The mixture was ice cooled and was vacuum filtered and the recovered product was washed with a 1-4 ethanol-ether mixture to obtain 5.34 g of the desired hydrochloride melting at 198° C.

EXAMPLE 18

Tablets were prepared in the usual manner containing 50 mg of either the product of Example 1 or Example 14 and sufficient excipient of lactose, starch, talc and mangnesium stearate for a final weight of 350 mg.

PHARMACOLOGICAL DATA

Analgesic Activity

The test used was based on that of Koster et al [Fed. Proc., Vol. 18 (1959), p 412] in which mice received an intraperitoneal injection of acetic acid to provoke repeated stretching and twisting movements which persisted for more than 6 hours. Analgesics prevent or diminish this syndrome which is considered to be the exteriorization of a diffuse abdominal pain. The solution of 1% acetic acid in water was used and the dose which declenched this syndrome due to the administration of 0.01 ml/g or 100 mg/kg of acetic acid was determined. The test products were orally administered 30 minutes before the acetic acid injection and the mice were kept without food from the day before the tests. The stretchings were observed and counted for each mouse for a period of 15 minutes starting right after the acetic acid injection. The $DA_{50}$, the dose which diminished the symptoms by 50% as compared to the controls, was determined and the results are reported in Table I.

TABLE I

| Product of Example | $DA_{50}$ in mg/kg |
|---|---|
| 1 | 10 |
| 3 | 10 |
| 12 | 4 |
| 13 | 10 |
| 14 | 3 |
| 15 | 3 |
| 16 | 8 |

The results of Table I show that the tested products have good analgesic activity.

Various modifications of the products and methods of the invention may be made without departing from the spirit or scope thereof and it should be understood that the invention is intended to be limited only as defined in the appended claims.

We claim:

1. A compound selected from the group consisting of 2-(4-quinolinylamino)-5-fluoro-benzoic acid compounds of the formula wherein X is selected from the group consisting of chlorine and —$CF_3$ in the 7- or 8-position and R is selected from the group consisting of hydrogen, alkyl of 1 to 8 carbons, $$-A-N\begin{matrix}R_1\\R_2\end{matrix}$$

wherein A is branched alkylene of 3 to 5 carbon atoms or —$(CH_2)_n$— and n is a number of 2 to 5 and $R_1$ and $R_2$ are individually alkyl of 1 to 8 carbon atoms or together with the nitrogen atom to which they are attached form a heterocyclic selected from the group consisting of piperidinyl, pyrrolidinyl, morpholinyl and N-piperazinyl optionally substituted on the second nitrogen atoms with alkyl of 1 to 4 carbon atoms, with $R_3$ being selected from the group consisting of hydrogen, halogen, —$CF_3$, —$SCF_3$, —$OCF_3$ and alkyl and alkoxy of 1 to 8 carbon atoms in the 2,3- or 4-position, n' is 2 to 5 and $$-CH_2-\underset{OR_4}{CH}-\underset{OR_5}{CH_2}$$

and $R_4$ and $R_5$ are both hydrogen or form a ketonide of the formula

and P and Q are alkyl of 1 to 8 carbon atoms, phenylalkyl of 7 to 13 carbon atoms or phenyl, alkali metals, alkaline earth metals, ammonium and non-toxic, pharmaceutically acceptable organic amines and their non-toxic, pharmaceutically acceptable acid addition salts.

2. A compound of claim 1 wherein R is selected from the group consisting of hydrogen, —NH$_4$, alkali metals, alkaline earth metals and a non-toxic, pharmaceutically acceptable organic amine.

3. A compound of claim 1 wherein R is selected from the group consisting of methyl,

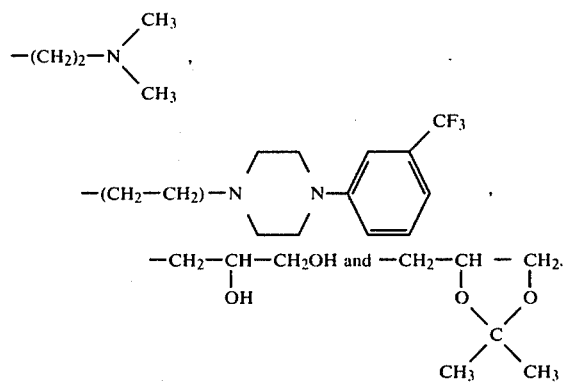

4. A compound of claim 1 wherein X is 7-chloro.
5. A compound of claim 1 wherein X is the 8-position.
6. A compound of claim 5 wherein X is —CF$_3$.
7. A compound of claim 1 selected from the group consisting of methyl 2-(7-chloro-4-quinolinylamino)-5-fluorobenzoate, (2,2-dimethyl-4-dioxalyl)-methyl 2-(8-trifluoromethyl-4-quinolinylamino)-5-fluoro-benzoate, 2-dimethylaminoethyl 2-(8-trifluoromethyl-4-quinolinylamino)-5-fluorobenzoate and its hydrochloride, 2-[4-(3-trifluoromethylphenyl)-piperazin-1-yl]-ethyl 2-(8-trifluoromethyl-4-quinolinylamino)-5-fluoro-benzoate and its hydrochloride and 2,3-dihydroxypropyl 2-(8-trifluoromethyl-4-quinolinylamino)-5-fluoro-benzoate.

8. An analgesic composition comprising an analgesically effective amount of at least one compound of claim 1 and an excipient.

9. A composition of claim 8 wherein R is selected from the group consisting of hydrogen, —NH$_4$, alkali metals, alkaline earth metals, and a non-toxic, pharmaceutically acceptable organic amine.

10. A composition of claim 8 wherein R is selected from the group consisting of methyl,

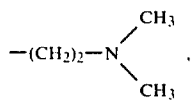

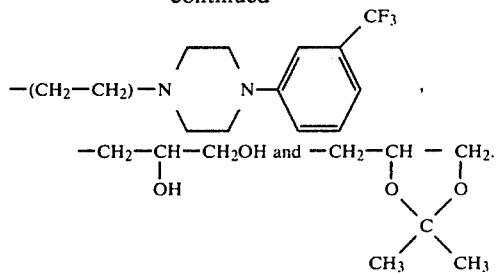

11. A composition of claim 8 wherein X is 7-chloro.
12. A composition of claim 8 wherein X is in the 8-position.
13. A composition of claim 12 wherein X is —CF$_3$.
14. A composition of claim 8 selected from the group consisting of methyl 2-(7-chloro-4-quinolinylamino)-5-fluorobenzoate, (2,2-dimethyl-4-dioxalyl)-methyl 2-(8-trifluoromethyl-4-quinolinylamino)-5-fluoro-benzoate, 2-dimethylaminoethyl 2-(8-trifluoromethyl-4-quinolinylamino)-5-fluorobenzoate and its hydrochloride, 2-[(3-trifluoromethylphenyl)-piperazin-yl]-ethyl 2-(8-trifluoromethyl-4-quinolinylamino)-5-fluoro-benzoate and its hydrochloride and 2,3-dihydroxypropyl 2-(8-trifluoromethyl-4-quinolinylamino)-5-fluoro-benzoate.

15. A method of relieving pain in warm-blooded animals comprising administering to warm-blooded animals an analgesically effective amount of at least one compound of claim 1.

16. A method of claim 15 wherein R is selected from the group consisting of hydrogen, —NH$_4$, alkali metals, alkaline earth metals and a non-toxic, pharmaceutically acceptable organic amine.

17. A method of claim 15 wherein R is selected from the group consisting of methyl,

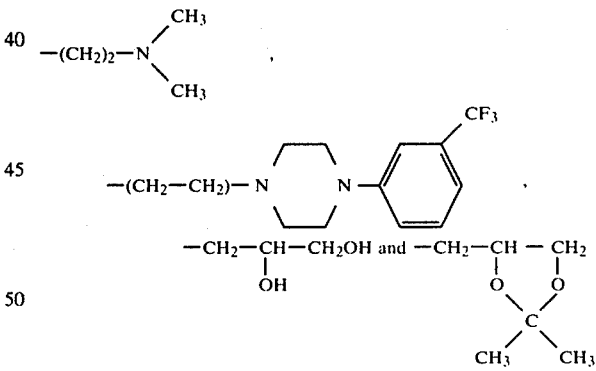

18. A method of claim 15 wherein X is 7-chloro.
19. A method of claim 15 wherein X is in the 8-position.
20. A method of claim 19 wherein X is —CF$_3$.
21. A method of claim 15 selected from the group consisting of methyl 2-(7-chloro-4-quinolinylamino)-5-fluorobenzoate, (2,2-dimethyl-4-dioxalyl)-methyl 2-(8-trifluoromethyl-4-fluoro-benzoate, 2-dimethylaminoethyl 2-(8-trifluoromethyl-4-quinolinylamino)-5-fluorobenzoate and its hydrochloride, 2-[4-(3-trifluoromethylphenyl)-piperazin-1-yl]-ethyl 2-(8-trifluoromethyl-4-quinolinylamino)-5-fluoro-benzoate and its hydrochloride and 2,3-dihydroxypropyl 2-(8-trifluoromethyl-4-quinolinylamino)-5-fluoro-benzoate.

* * * * *

UNITED STATES PATENT AND TRADEMARK OFFICE
CERTIFICATE OF CORRECTION

PATENT NO. : 4,233,305
DATED : November 11, 1980
INVENTOR(S) : ANDRE ALLAIS ET AL.

It is certified that error appears in the above—identified patent and that said Letters Patent is hereby corrected as shown below:

Column 6, line 12: "2-fluoro-benzoate" should read

-- 2-amino-5-fluoro-benzoate --"

Column 6, line 45: "was added" should read -- were added --.

Column 14, line 23: 2-[(3-trifluoro ..." should read

-- 2-[4-(3-trifluoro ... --

Column 14, line 61: " 4-fluoro-benzoate" should read

-- 4-quinolinylamino)-5-fluoro-benzoate --.

Signed and Sealed this

Fifth Day of May 1981

[SEAL]

Attest:

RENE D. TEGTMEYER

Attesting Officer   Acting Commissioner of Patents and Trademarks